United States Patent
Kuppuraj et al.

(10) Patent No.: US 10,376,172 B2
(45) Date of Patent: *Aug. 13, 2019

(54) SYSTEMS AND METHODS FOR CLASSIFYING AND DISPLAYING DATA

(71) Applicant: InfoBionic, Inc., Lowell, MA (US)

(72) Inventors: Ravi Kuppuraj, Andover, MA (US); Serban P. Georgescu, Natick, MA (US); Michael Fahey, Medway, MA (US); Juhan Sonin, Arlington, MA (US); Eric Benoit, Cambridge, MA (US)

(73) Assignee: INFOBIONIC, INC., Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,265

(22) Filed: Mar. 10, 2016

(65) Prior Publication Data
US 2016/0183833 A1 Jun. 30, 2016

Related U.S. Application Data

(63) Continuation of application No. 14/731,050, filed on Jun. 4, 2015, now Pat. No. 9,307,922, which is a
(Continued)

(51) Int. Cl.
*A61B 5/044* (2006.01)
*A61B 5/0452* (2006.01)
(Continued)

(52) U.S. Cl.
CPC .......... *A61B 5/0452* (2013.01); *A61B 5/0006* (2013.01); *A61B 5/0022* (2013.01);
(Continued)

(58) Field of Classification Search
None
See application file for complete search history.

(56) References Cited

U.S. PATENT DOCUMENTS

| 2,190,543 | A | 2/1940 | Ivie et al. |
| 4,625,278 | A | 11/1986 | Wong |

(Continued)

FOREIGN PATENT DOCUMENTS

| EP | 1 304 072 A2 | 4/2003 |
| WO | WO 98/16895 A1 | 4/1998 |

(Continued)

OTHER PUBLICATIONS

Craig Robinson, "Flip Flop Fly Ball—Height of MLB Players," http://blogs.thescore.com/mlb/2012/06/14/flip-flop-fly-ball-height-of-mlb-players/, Jun. 2012.*
(Continued)

*Primary Examiner* — Kennedy Schaetzle
(74) *Attorney, Agent, or Firm* — Bookoff McAndrews, PLLC

(57) ABSTRACT

A method is disclosed for displaying patient ECG data. The method includes receiving ECG data including an ECG waveform; receiving analyzed ECG data including arrhythmic events; generating an indicia of the detected arrhythmic event; and displaying the indicia of the detected arrhythmic event in relation to the ECG waveform at a position associated with a time of the detected arrhythmic event. A system for displaying patient ECG data is also disclosed.

20 Claims, 10 Drawing Sheets

Related U.S. Application Data continuation of application No. 14/316,068, filed on Jun. 26, 2014, now Pat. No. 9,081,884, which is a continuation of application No. 14/088,950, filed on Nov. 25, 2013, now Pat. No. 8,798,734, which is a continuation of application No. 13/763,180, filed on Feb. 8, 2013, now Pat. No. 8,620,418.

(60) Provisional application No. 61/749,052, filed on Jan. 4, 2013.

(51) Int. Cl.
*A61B 5/00* (2006.01)
*A61B 5/0464* (2006.01)
*A61B 5/0404* (2006.01)
*A61B 5/04* (2006.01)
*G16H 50/20* (2018.01)
*G06F 19/00* (2018.01)
*G16H 15/00* (2018.01)

(52) U.S. Cl.
CPC .......... *A61B 5/044* (2013.01); *A61B 5/0404* (2013.01); *A61B 5/04012* (2013.01); *A61B 5/0464* (2013.01); *A61B 5/4842* (2013.01); *A61B 5/7246* (2013.01); *A61B 5/7264* (2013.01); *G16H 50/20* (2018.01); *G06F 19/3418* (2013.01); *G16H 15/00* (2018.01)

(56) References Cited

U.S. PATENT DOCUMENTS

| | | | |
|---|---|---|---|
| 5,305,202 A | 4/1994 | Gallant et al. | |
| 5,724,985 A | 3/1998 | Snell et al. | |
| 6,748,274 B2 | 6/2004 | Levine et al. | |
| 6,951,516 B1 | 10/2005 | Eguchi et al. | |
| 7,174,205 B2 | 2/2007 | Moreno et al. | |
| 8,321,006 B1 | 11/2012 | Snyder et al. | |
| 8,400,436 B1 | 3/2013 | Kuck et al. | |
| 8,620,418 B1 | 12/2013 | Kuppuraj et al. | |
| 8,790,255 B2 | 7/2014 | Behar | |
| 9,307,922 B2* | 4/2016 | Kuppuraj | A61B 5/0404 |
| 2001/0008954 A1 | 7/2001 | Levitan et al. | |
| 2005/0076060 A1 | 4/2005 | Finn et al. | |
| 2006/0074321 A1 | 4/2006 | Kouchi et al. | |
| 2008/0009684 A1 | 1/2008 | Corsetti et al. | |
| 2009/0054735 A1 | 2/2009 | Higgins et al. | |
| 2009/0054743 A1 | 2/2009 | Stewart | |
| 2009/0144639 A1* | 6/2009 | Nims | A63B 24/0059 715/757 |
| 2009/0156907 A1* | 6/2009 | Jung | A61B 5/0476 600/300 |
| 2009/0228298 A1 | 9/2009 | Xue | |
| 2009/0299150 A1 | 12/2009 | Alberte, Jr. et al. | |
| 2010/0299155 A1 | 11/2010 | Findlay et al. | |
| 2011/0133444 A1* | 6/2011 | Doiron | A61J 7/04 283/74 |
| 2011/0218406 A1* | 9/2011 | Hussain | A61B 5/14551 600/300 |
| 2011/0275942 A1 | 11/2011 | Stahmann et al. | |
| 2013/0085403 A1 | 4/2013 | Gunderson et al. | |
| 2013/0151275 A1* | 6/2013 | Thiers | G06F 19/327 705/2 |
| 2013/0211214 A1* | 8/2013 | Olsen | A61B 5/742 600/316 |
| 2014/0073486 A1* | 3/2014 | Ahmed | A61B 5/02405 482/9 |
| 2014/0227450 A1* | 8/2014 | Hironimus | B05C 17/00516 427/429 |

FOREIGN PATENT DOCUMENTS

| | | |
|---|---|---|
| WO | WO 2005/101227 A1 | 10/2005 |
| WO | WO 2009/005734 A2 | 1/2009 |
| WO | WO 2009/033010 A1 | 3/2009 |
| WO | WO 2011/001302 A1 | 1/2011 |

OTHER PUBLICATIONS

International Search Report issued in corresponding International Application No. PCT/US2013/077664, dated Apr. 10, 2014.

* cited by examiner

SYSTEMS AND METHODS FOR CLASSIFYING AND DISPLAYING DATA

RELATED APPLICATIONS

This application is a continuation of U.S. patent application Ser. No. 14/731,050, filed Jun. 4, 2015, now U.S. Pat. No. 9,307,922 (issued Apr. 12, 2016), which is a continuation of U.S. application Ser. No. 14/316,068, filed Jun. 26, 2014, now U.S. Pat. No. 9,081,884 (issued Jul. 14, 2015), which is a continuation of U.S. patent application Ser. No. 14/088,950, filed Nov. 25, 2013, now U.S. Pat. No. 8,798,734 (issued Aug. 5, 2014), which is a continuation of U.S. patent application Ser. No. 13/763,180, filed Feb. 8, 2013, now U.S. Pat. No. 8,620,418 (issued Dec. 31, 2013), which claims priority to U.S. Provisional Patent Application No. 61/749,052, filed on Jan. 4, 2013, the entire disclosures of which are incorporated herein by reference.

TECHNICAL FIELD

Various embodiments of the present disclosure relate generally to displaying patient health data. More specifically, particular embodiments of the present disclosure relate to systems and methods for obtaining and processing patient health data, such as electrocardiograph (ECG) data, and displaying the data to a healthcare professional on a handheld device.

BACKGROUND

Remote monitoring of ambulatory patients enables doctors to detect or diagnose heart problems, such as arrhythmias, that may produce only transient symptoms and, therefore, may not be evident when the patients visit the doctors' offices. Several forms of cardiac event monitors have been used.

A "Holter" monitor is worn by a patient and collects and stores data for a period of time, typically at least 24 hours, and in some cases up to two weeks. After the data has been collected, the Holter monitor is typically brought or sent to a doctor's office, laboratory or the like, and the data is retrieved from the monitor and analyzed. Holter monitors are relatively inexpensive, but they cannot be used for real-time analysis of patient data, because the data is analyzed hours, days or weeks after it has been collected.

More timely analysis of heart data is made possible by pre-symptom (looping memory) event monitors. Such a device collects and stores patient data in a "loop" memory device that constantly overwrites previously stored data with newly collected data. The event monitor may include a button, which the patient is instructed to actuate if the patient feels ill or otherwise detects a heart-related anomaly. In response, the event monitor continues to record data for a short period of time and then stops recording, thereby retaining data for a time period that spans the button actuation. The retained data may then be sent via a modem and a telephone connection to a doctor's office or to a laboratory for analysis.

Mobile Cardiac Telemetry (MCT) refers to a technique that involves noninvasive ambulatory cardiac event monitors that are capable of continuous measurements of heart rate and rhythm over several weeks. For example, some MCT devices include an automatic electrocardiograph (ECG) arrhythmia detector that couples to a cellular telephone device to immediately transmit automatically detected abnormal ECG waveforms to a remote monitoring center, which can then alert a physician. Such devices also include a memory capable of storing ECG waveform data, which is transmitted to a cellular phone for analysis, and then to the remote monitoring center whenever an event is detected by the smartphone algorithms. Although data about automatically detected arrhythmias is sent immediately to the remote monitoring center, without requiring patient action, the computational resources and corresponding electrical power (battery) required to perform the automatic ECG analysis in the device are significant.

Some MCT devices continuously send all collected ECG data to a remote monitoring center for analysis. These MCT devices typically do not perform any ECG analysis of their own. Although no patient-initiated action is required, the large amount of data transmitted by the MCT wireless devices consumes more of the wireless bandwidth used to convey the data. Furthermore, a large amount of computational resources is required at the remote monitoring center to analyze the continuous stream of received data, especially when many patients are monitored by a single data center.

To improve the collection, transmission and processing of physiological data, InfoBionic of Lowell, MA has developed a novel system that collects high definition physiologic data, but sends a downsampled version of it to a remote server for the first-pass processing. When the remote server detects an arrhythmia, it requests the high resolution data from the transceiver for a second-pass analysis. Embodiments of this system are disclosed in U.S. patent application Ser. No. 13/446,490, filed on Apr. 13, 2012, the entirety of which is hereby incorporated herein by reference.

However, to date, regardless of how much ECG data is collected and analyzed, and whether ECG data is analyzed on a local or remote device, the resulting ECG data is typically presented to physicians in long, printed reports. Such printed reports of ECG data are static, and therefore do not include the latest ECG data obtained from a patient device, and are also not able to be manipulated by a reviewing physician. Moreover, printed reports are tedious to review and difficult to understand, which makes physicians less interested in reviewing those reports. As a result, review of printed reports of ECG data is sometimes delayed and/or delegated to junior physicians. Thus, while the systems and methods of the '490 application address certain challenges associated with the collection and analysis of immense amounts of ECG data, a need remains for improved systems and methods for reporting and displaying collected and processed ECG data for a plurality of patients to healthcare professionals.

SUMMARY OF THE DISCLOSURE

A method is disclosed for displaying patient ECG data. The method includes receiving ECG data including an ECG waveform; receiving analyzed ECG data to detect an arrhythmic event experienced by the patient; generating an indicia of the detected arrhythmic event; and displaying the indicia of the detected arrhythmic event in relation to the ECG waveform at a position associated with a time of the detected arrhythmic event.

The indicia of the detected arrhythmic event includes an indication of a detected severity of the detected arrhythmic event or an indication of a detected recency of the detected arrhythmic event. The indicia of the detected arrhythmic event has a size that increases based on a detected severity of the detected arrhythmic event, or a color or shape that changes based on a detected severity of the detected arrhythmic event.

The method further includes classifying the patient into one of a plurality of patient groups based on a detected severity or a detected recency of the detected arrhythmic event. The plurality of patient groups include: a first group of patients that have experienced a recent arrhythmic event, a second group of patients that have not experienced a recent arrhythmic event and a third group of patients that have completed a prescribed monitoring period. The method further includes generating a group indicia associated with each of the plurality of patient groups; wherein a size of a group indicia associated with the first group of patients is bigger than a size of a group indicia associated with the second group of patients, or a color of a group indicia associated with the first group of patients is brighter than a color of a group indicia associated with the second group of patients.

The method further includes generating a group indicia associated with each of the plurality of patient groups; and displaying the plurality of group indicia, each group indicia including an identification of one or more patients classified into the patient group of the group indicia. A color, shape, or size of each group indicia is changed based on a number of patients classified in the group, or a number or a severity of one or more detected arrhythmic events of patients classified in the group.

The method further includes generating a display of indicia of a plurality of patients, each indicia of each of the plurality of patients including an ECG waveform and indicia of a detected arrhythmic event associated with each respective patient; and sorting the displayed indicia of the plurality of patients based on a classifying of each of the plurality of patients into one of the plurality of patient groups. The method further includes generating a display of indicia of a plurality of patients, each indicia of each of the plurality of patients including an ECG waveform and indicia of a detected arrhythmic event associated with each respective patient; and sorting a sequence of the displayed indicia of the plurality of patients based on a number, a recency, or a severity of one or more detected arrhythmic events for each patient.

The ECG data is received from a sensor associated with a patient. The method further includes receiving, from a physician, a request to view the ECG data; and transmitting, to the physician, one or more images that displays the indicia of the detected arrhythmic event in relation to the ECG waveform at a position associated with a time of the detected arrhythmic event.

The method further includes generating a group indicia associated with each of the plurality of patient groups, each group indicia being representative of a planet or astronomical object in the universe, and displaying the plurality of group indicia, each group indicia including an identification of one or more patients classified into the patient group of the group indicia.

A system is disclosed for displaying patient ECG data. The system includes a data storage device storing instructions for displaying patient ECG data; and a processor configured to execute the instructions to perform a method comprising: receiving ECG data including an ECG waveform; receiving analyzed ECG data to detect an arrhythmic event experienced by the patient; generating an indicia of the detected arrhythmic event; and displaying the indicia of the detected arrhythmic event in relation to the ECG waveform at a position associated with a time of the detected arrhythmic event.

The indicia of the detected arrhythmic event includes an indication of a detected severity of the detected arrhythmic event or an indication of a detected recency of the detected arrhythmic event. The indicia of the detected arrhythmic event has a size that increases based on a detected severity of the detected arrhythmic event, or a color or shape that changes based on a detected severity of the detected arrhythmic event.

The processor is further configured for: classifying the patient into one of a plurality of patient groups based on a detected severity or a detected recency of the detected arrhythmic event. The plurality of patient groups include: a first group of patients that have experienced a recent arrhythmic event, a second group of patients that have not experienced a recent arrhythmic event, and a third group of patients that have completed a prescribed monitoring period.

The processor is further configured for: generating a group indicia associated with each of the plurality of patient groups; wherein a size of a group indicia associated with the first group of patients is bigger than a size of a group indicia associated with the second group of patients, or a color of a group indicia associated with the first group of patients is brighter than a color of a group indicia associated with the second group of patients.

The processor is further configured for: generating a group indicia associated with each of the plurality of patient groups; and displaying the plurality of group indicia, each group indicia including an identification of one or more patients classified into the patient group of the group indicia. A color, shape, or size of each group indicia is changed based on a number of patients classified in the group, or a number or a severity of one or more detected arrhythmic events of patients classified in the group.

The processor is further configured for: generating a display of indicia of a plurality of patients, each indicia of each of the plurality of patients including an ECG waveform and indicia of a detected arrhythmic event associated with each respective patient; and sorting the displayed indicia of the plurality of patients based on a classifying of each of the plurality of patients into one of the plurality of patient groups.

The processor is further configured for: generating a display of indicia of a plurality of patients, each indicia of each of the plurality of patients including an ECG waveform and indicia of a detected arrhythmic event associated with each respective patient; and sorting a sequence of the displayed indicia of the plurality of patients based on a number, a recency, or a severity of one or more detected arrhythmic events for each patient.

The ECG data is received from a sensor associated with a patient. The processor is further configured for: receiving, from a physician, a request to view the ECG data; and transmitting, to the physician, one or more images that displays the indicia of the detected arrhythmic event in relation to the ECG waveform at a position associated with a time of the detected arrhythmic event.

The processor is further configured for generating a group indicia associated with each of the plurality of patient groups, each group indicia being representative of a planet or astronomical object in the universe, and displaying the plurality of group indicia, each group indicia including an identification of one or more patients classified into the patient group of the group indicia.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
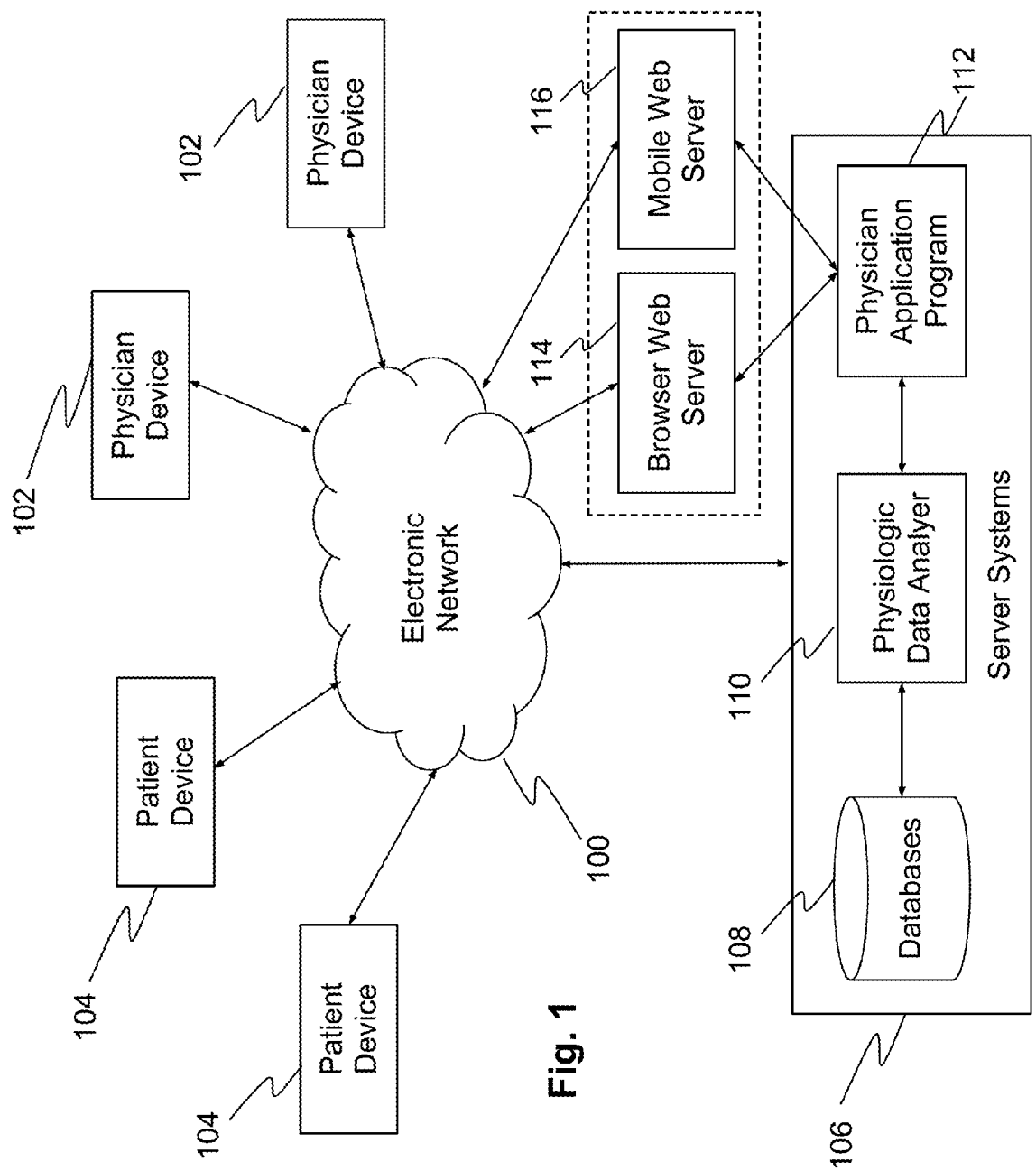
FIG. 1 is a schematic diagram of a system and environment for collecting, processing, and displaying ECG data, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

In view of the challenges outlined above, systems and methods are disclosed for remote physiologic monitoring of a body of a patient, in association with a remote server. In one embodiment, the system may include a plurality of sensors and a transceiver assembly. Each sensor of the plurality of sensors may be configured to be coupled to the body of the patient to generate respective physiologic data about the body. The transceiver assembly may include a memory, a controller and a wireless transceiver. The transceiver assembly may be communicatively coupled to the plurality of sensors. The transceiver assembly may be configured to receive the physiologic data from the plurality of sensors. The transceiver assembly may also be configured to store the received physiologic data in the memory.

In one embodiment, the transceiver and sensors may be configured to collect patient ECG data according to the embodiments and methods described in the '490 application (described above and incorporated herein by reference). In particular, the transceiver assembly may be configured to send a subset of the received physiologic data (referred to as "less detailed data"), via the wireless transceiver, to the remote server. The less detailed data sent to the remote server may be characterized by a lower resolution than some "more detailed data" stored in the memory for a corresponding time period and/or a lower sampling rate than the more detailed data stored in the memory for a corresponding time period, and/or having been received from a different set of the sensors than the more detailed data stored in the memory for a corresponding time period. The transceiver assembly may be configured to fetch at least a portion of the more detailed physiologic data from the memory, in response to a signal from the remote server. In addition, in response to the signal from the remote server, the transceiver assembly is configured to send the fetched more detailed physiologic data to the remote server. The remote server may be configured to receive the less detailed physiologic data sent by the transceiver assembly and automatically analyze the received less detailed physiologic data for an indication of a health-related anomaly. If the health-related anomaly is indicated, the remote server may be configured to automatically send the signal to the transceiver assembly. The health-related anomaly may be or include an arrhythmia. In one embodiment, the wireless transceiver assembly may include a cellular telephone coupled via a short-range wireless link to the wireless transceiver. The cellular telephone may be configured to store the more detailed data in the memory, send the less detailed data to the remote server, responsive to the signal, fetch the at least the portion of the more detailed physiologic data from the memory, and send the fetched more detailed physiologic data to the remote server via a wireless carrier network. Although, the presently disclosed embodiments may be used with the "more detailed data" and "less detailed data" collection scheme described above and in the '490 application, the presently disclosed embodiments may be used in relation to any remote arrhythmia detection system, regardless of the quantity of ECG or arrhythmia data collected.

Referring now to the enclosed figures, FIG. 1 is a schematic diagram of a system and environment for collecting, processing, and displaying ECG data, according to an exemplary embodiment of the present disclosure. As shown in FIG. 1, the system and environment may include a plurality of physician devices 102 and patient devices 104 disposed in communication with an electronic network 100. Electronic network 100 may be the Internet, or any other combination of wired and/or wireless electronic networks.

In one embodiment, each of physician devices 102 may include a server, personal computer, tablet computer, mobile device, smartphone, and/or personal digital assistant ("PDA") disposed in communication with electronic network 100. For example, in one embodiment, each of physician devices 102 may be a touchscreen enabled device, such as an Apple iPad, Samsung Galaxy, Amazon Kindle, Microsoft Surface, or any other equivalent or similar device. Each of physician devices 102 may have a web browser or mobile browser installed for receiving and displaying content from web servers. Thus, each of physician devices 102 may be configured to receive and display data that is received and processed from patient devices 104, over electronic network 100.

In one embodiment, each of patient devices 104 may include a combination of physiologic sensors, a memory, a battery, and/or a transceiver, one or more of which may be disposed within or in communication with a mobile device, such as a smartphone, PDA, or other handheld or wearable electronic device. In one embodiment, the physiologic sensors may be disposed in short-range wireless, Bluetooth, radio-frequency (RFID), and/or near-field communications (NFC) communication with a mobile device carried or worn by the patient. Each of patient devices 104 may be connected to electronic network 100 through a cellular network and/or a Wi-Fi network. Thus, each of patient devices 104 may be configured to collect physiological data from a patient, and transmit collected physiological data over electronic network 100. Each of patient devices 104 may also have a web browser or mobile browser installed for receiving and displaying content from web servers.

As shown in FIG. 1, a plurality of server systems 106, a browser web server 114, and/or a mobile web server 116 may also be disposed in communication with electronic network 100. In one embodiment, server systems 106 may be configured to receive physiological data from patient devices 104 over electronic network 100. Any of the devices or functionality of server systems 106, browser web server 114, and/or a mobile web server 116 may be combined together or separated, and may be operated by a single administrative entity, or outsourced to one or more other entities, such as a web hosting entity, web storage entity, and/or cloud computing service.

As shown in the embodiment of FIG. 1, server systems 106 may include a physiological data analyzer 110, which may be configured to perform high-sensitivity analysis and high specificity analysis on received physiological data. Specifically, physiological data analyzer 110 may be configured to analyze received physiological data for detecting arrhythmic events, determine a severity of any detected arrhythmic events, and/or perform any other analysis, classification, and/or sorting of detected arrhythmic events and/or patients having experienced arrhythmic events, as will be described in more detail below.

Server systems 106 may also include one or more databases 108, where data analyzer 110 may be configured to store the received physiological data. As described above with respect to the '490 application, server system 106 may be configured to receive and store either "less detailed data" and/or "more detailed data," or a portion thereof. Any received data may be stored in the databases 108 in an encrypted form to increase security of the data against unauthorized access.

Server systems 106 may also include a physician application program 112 that allows a physician to control parameters of the system, such as threshold values used by the data analyzer 110 in performing high-sensitivity and/or high-specificity analyses. The physician application program 112 also displays data to the physician and allows the physician to select types of data to display, time periods of the data to display, levels of data detail to display and other operating parameters of the system. For example, the physician may select a beginning and ending time surrounding a suspected or verified arrhythmia for display. In response to a query by the physician, the physician application program 112 may fetch and display data from the databases 108. If the requested data is not available in the databases 108, or if the requested data is not available in the database 108 at the level of detail requested by the physician, the physician application program 112 may automatically communicate with the transceiver of a patient device 104 to fetch the appropriate data in the appropriate amount of detail.

The physician application program 112 may implement appropriate security protocols, such as requiring the physician to enter logon credentials, so as to appropriately limit access to patient data and comply with regulations, such as the Health Insurance Portability and Accountability Act (HIPAA).

As shown in FIG. 1, server systems 106 may be disposed in communication with a browser web server 114 and/or a mobile web server 116. Each of browser web server 114 and/or mobile web server 116 may be configured to interact with physician devices 102, such as to accept user (physician, patient or administrator) inputs and generate appropriate displays to facilitate user interaction with the physician application program 112. For example, browser web server 114 and/or mobile web server 116 may be configured to generate a window-metaphor based computer user interface on a screen of physician device(s) 102 or screen (not shown) coupled to the remote server systems 106, or the browser web server 114 and/or mobile web server 116 may generate web pages that are rendered by a browser or application of the physician devices 102. The physician devices 102 and the browser web server 114 and/or mobile web server 116 may communicate with each other using an appropriate encrypted protocol, such as Hypertext Transfer Protocol Secure (HTTPS).

Figure 2:
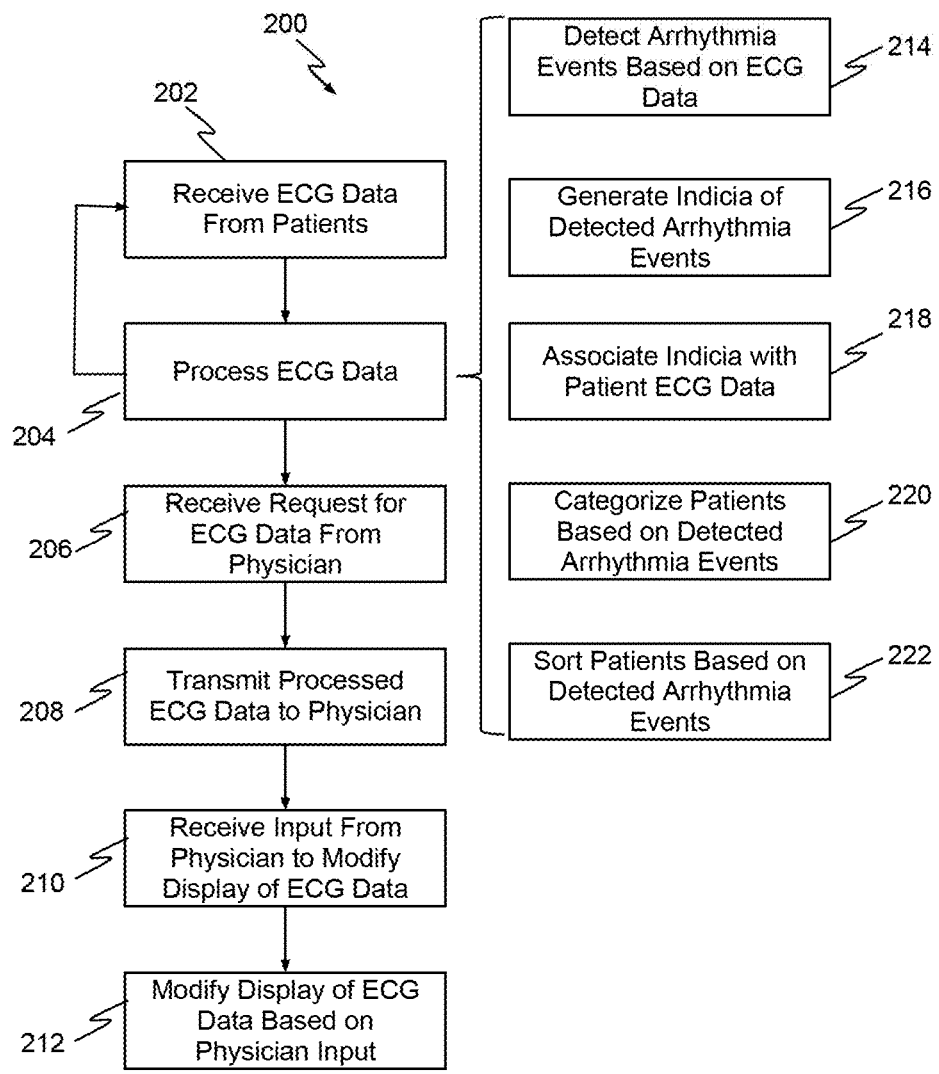
FIG. 2 is a flow diagram of a method for collecting, processing, and displaying ECG data, according to an exemplary embodiment of the present disclosure.

FIG. 2 is a flow diagram of a method 200 for collecting, processing, and displaying ECG data, e.g., using the exemplary system and devices of FIG. 1, according to an exemplary embodiment of the present disclosure. As shown in FIG. 2, method 200 may initially include receiving ECG data from one or more patients (step 202). For example, server systems 106 may receive ECG data from one or more patient devices 104, which may then be stored in databases 108. In one embodiment, patient devices 104 may include or may be disposed in communication with a plurality of sensors.

Figure 3:
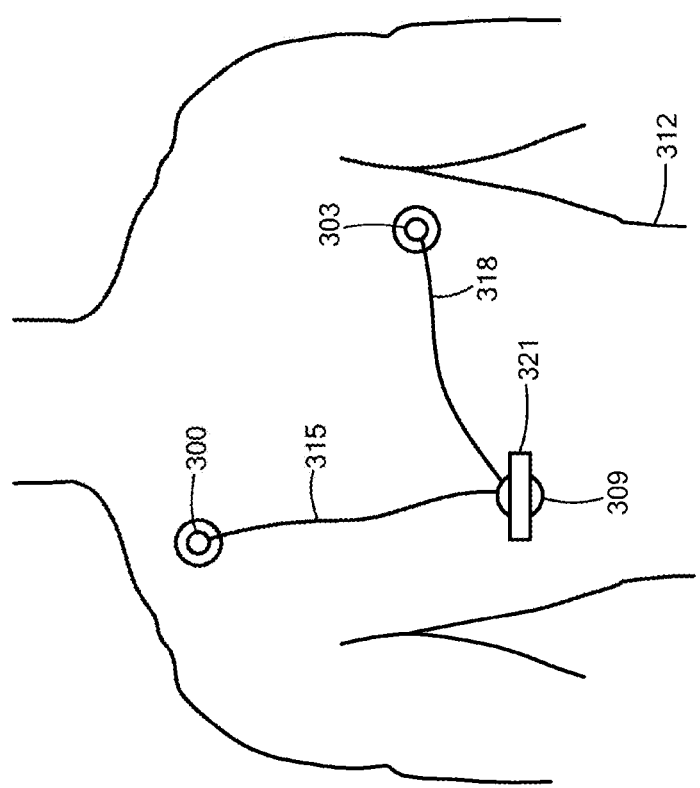
FIG. 3 is a schematic diagram of a device, e.g., sensors, positioned on a patient torso for collecting patient ECG data, according to an exemplary embodiment of the present disclosure.

FIG. 3 is a schematic diagram of a device, e.g., sensors, positioned on a patient torso for collecting patient ECG data, according to an exemplary embodiment of the present disclosure. Specifically, FIG. 3 is a schematic diagram illustrating one possible combination of physiological sensors 300, 303 and 309 and a possible placement of the sensors on a torso 312 of a patient. One of the sensors 309 may be attached at about the elevation of the diaphragm of the patient. Each sensor 300-309 may be attached to the torso 312 using known gel pads or other conventional attachment techniques. Any combination of known physiological electrodes may be used for the sensors 300-309. For example, the sensors 300-309 may include any combination of SpO2 sensors, blood pressure sensors, ECG electrodes, respiration sensors, movement and activity sensors, and the like. Movement or activity may be sensed with appropriate accelerometers or gyroscopes, such as micro electro-mechanical system (MEMS) devices. The sensors 300-309 may be connected via wires or optical cables 315 and 318 or via wireless links, such as Bluetooth links. Respiration data may be derived from ECG baseline data, as is known to those of skill in the art. Optionally, other sensors, such as a patient weight measuring device, blood pressure cuff, etc., may be disconnectably coupled via wires, optical cables or wirelessly to a transceiver assembly of patient devices 104. Thus, as discussed above, patient devices 104 may be configured to collect physiologic data, store the collected data in a memory, and send a full detail or less-detailed version of the data to the remote server systems 106 for storage in databases 108.

Referring now back to FIG. 2, method 200 may then include processing the received ECG data (step 204). In one embodiment, processing the received ECG data may include detecting arrhythmic events (step 214). For example, the ECG data may be processed by the data analyzer 110 to automatically classify heartbeats using morphology and heartbeat interval features, as described by Philip de Chazal, et al., in "Automatic Classification of Heartbeats Using ECG Morphology and Heartbeat Interval Features," IEEE Transactions on Biomedical Engineering, Vol. 51, No. 7, July, 2004, the contents of which are hereby incorporated by reference. In other words, collected data may be processed before a determination is made whether an anomaly has been detected. As noted, arrhythmia may be suspected or verified (or both) using ECG data, non-ECG data, or a combination thereof. For example, an arrhythmia may be suspected or verified, based in whole or in part on respiration rate. The respiration rate may be determined based on data from one or more accelerometers in the sensors attached to the torso of the patient, as shown for example in FIG. 3. Chest movements detected by the accelerometers may be filtered, such as within expected frequencies and amplitudes, to derive the respiration rate. For example, one accelerometer may be included in the sensor 309 (FIG. 3), which is located adjacent the patient's diaphragm, and another accelerometer may be include in the sensor 300 or 303. Relative motion between the two locations on the torso 312 represented by the two accelerometers closely represents diaphragm movement and, therefore, breathing.

In addition to detecting arrhythmic events, the processing of the ECG data (of step 204) may also include generating an indicia of each detected arrhythmic event (step 216). For example, any type of indicia, such as an icon of a box, circle, planet, sphere, or any other shape may be generated to represent a detected arrhythmic event, as will be described in more detail below. In one embodiment, the generated indicia of the detected arrhythmic event may include an indication of a detected severity of the detected arrhythmic event or an indication of a detected recency of the detected arrhythmic event. In yet another embodiment, the generated indicia of the detected arrhythmic event may have a size that increases based on a detected severity of the detected arrhythmic event, or a color or shape that changes based on a detected severity of the detected arrhythmic event.

The processing of the ECG data (of step 204) may also include associating the generated indicia with patient ECG data (step 218). For example, indicia of a detected arrhythmic event may be displayed in relation to the ECG waveform of a patient, at a position associated with a time of the detected arrhythmic event.

The processing of the ECG data (of step 204) may also include categorizing patients based on the detected arrhythmic events (step 220). For example, method 200 may include classifying each patient into one of a plurality of patient groups based on a detected severity or a detected recency of the detected arrhythmic event. In one embodiment, the plurality of patient groups may include a first group of patients that have experienced a recent arrhythmic event, a second group of patients that have not experienced a recent arrhythmic event, and a third group of patients that have completed a prescribed monitoring period. In one embodiment, a size of a group indicia associated with the first group of patients may be bigger than a size of a group indicia associated with the second group of patients, or a color of a group indicia associated with the first group of patients may be brighter than a color of a group indicia associated with the second group of patients.

The processing of the ECG data (of step 204) may also include sorting patients based on the detected arrhythmic events (step 222). For example, method 200 may include generating a display of indicia of a plurality of patients, each indicia of each of the plurality of patients including an ECG waveform and indicia of any detected arrhythmic event associated with each respective patient, and sorting the displayed indicia of the plurality of patients based on a classifying of each of the plurality of patients into one of the plurality of patient groups. In one embodiment, method 200 may include sorting a sequence of the displayed indicia of the plurality of patients based on a number, a recency, or a severity of one or more detected arrhythmic events for each patient.

Method 200 may further include, either concurrently with or asynchronously from processing the ECG data, receiving a request for ECG data from a physician (step 206). For example, a physician may use a browser or other software installed on a physician device 102 to generate a request for ECG data from browser web server 114, mobile web server 116, and/or server systems 106. The physician may generate the request by simply manipulating a user interface, such as touching a user element associated with a patient for whom the physician desires to review ECG data. Alternatively, the physician may request ECG data for all of the physician's patients, or all of the patients of the physician's practice (e.g., the physician's patients and patients of the physician's partners, nurse practitioners, residents, supervising physicians, etc.).

Method 200 may further include transmitting the processed ECG data to a physician (step 208). For example, method 200 may include transmitting one or more images of ECG data and/or processed ECG data to the physician device 102 over electronic network 100. Transmission of ECG data may include displaying an ECG waveform for one or more patients to the physician. Transmission of ECG data may also include displaying indicia of detected arrhythmic events, indicia of groups of patients, and/or indicia of groups of arrhythmic events. For example, method 200 may include displaying to the physician a plurality of group indicia generated for each of a plurality of patient groups, where each group indicia may include an identification of one or more patients classified into the patient group of the group indicia.

Figure 4:
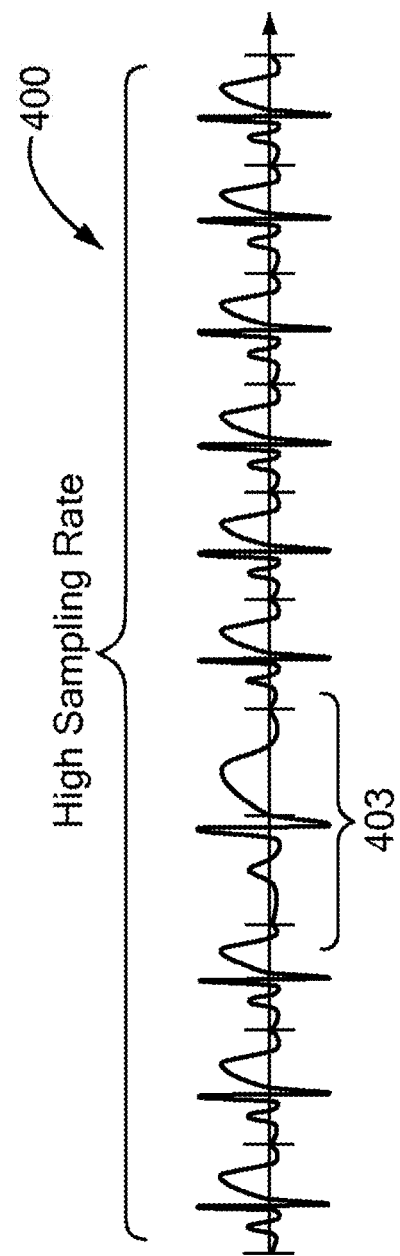
FIG. 4 is a schematic diagram of a portion of ECG data, reflected in a hypothetical ECG waveform of data collected by the system and methods of FIGS. 1-3, according to an exemplary embodiment of the present disclosure.

Method 200 may also include receiving an input from a physician to modify a display of ECG data (step 210). For example, method 200 may include receiving an input from a physician based on the physician's manipulation of a user element of a user interface of a physician device 102. In one embodiment, the input may include a swiping, squeezing, or pinching a display of an ECG waveform associated with a patient. FIG. 4 contains a hypothetical ECG waveform 400, representing detailed data collected from the sensors of patient devices 104. In one embodiment, the collected data may have a relatively high sampling rate and a relatively high resolution. Alternatively or additionally, the collected data may be down-sampled or have lower resolution. As shown in FIG. 4, the waveform 400 may include a portion 403, during which the waveform is anomalous, e.g., representing a detected arrhythmia.

Method 200 may then include modifying a display of ECG data based on received physician input (step 212). For example, a displayed waveform 400 may be advanced through time, expanded to cover more time, or compressed to "zoom in" on a shorter interval of time, as will be shown in more detail with respect to the exemplary physician interface screenshots of FIGS. 5-10.

Exemplary embodiments of an application operating on physician devices 102 will now be described with reference to the screenshots depicted in FIGS. 5-10. It will be appreciated that the screenshots are only exemplary, and that any desired user interface, touch interface mobile application, user elements, or manipulatable icons or shapes may be used to execute the method of FIG. 2.

Figure 5:
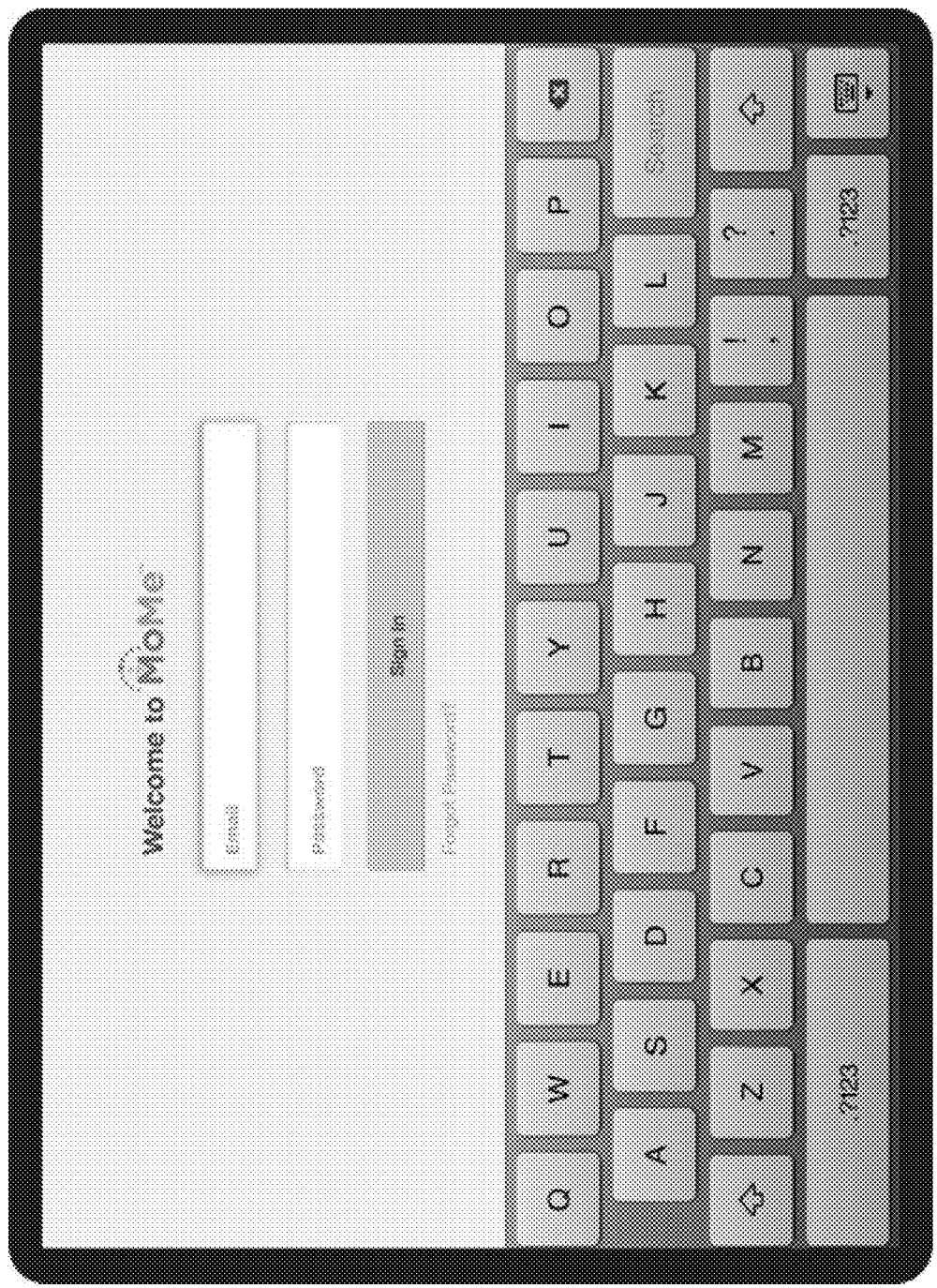
FIG. 5 is a screenshot of a physician interface for reviewing patient ECG data, according to an exemplary embodiment of the present disclosure.

FIG. 5 is a screenshot of a physician interface for logging into an application for reviewing patient ECG data. As discussed above, the log-in interface of FIG. 5 may appropriately limit access to patient data and comply with regulations, such as the Health Insurance Portability and Accountability Act (HIPAA).

Figure 6:
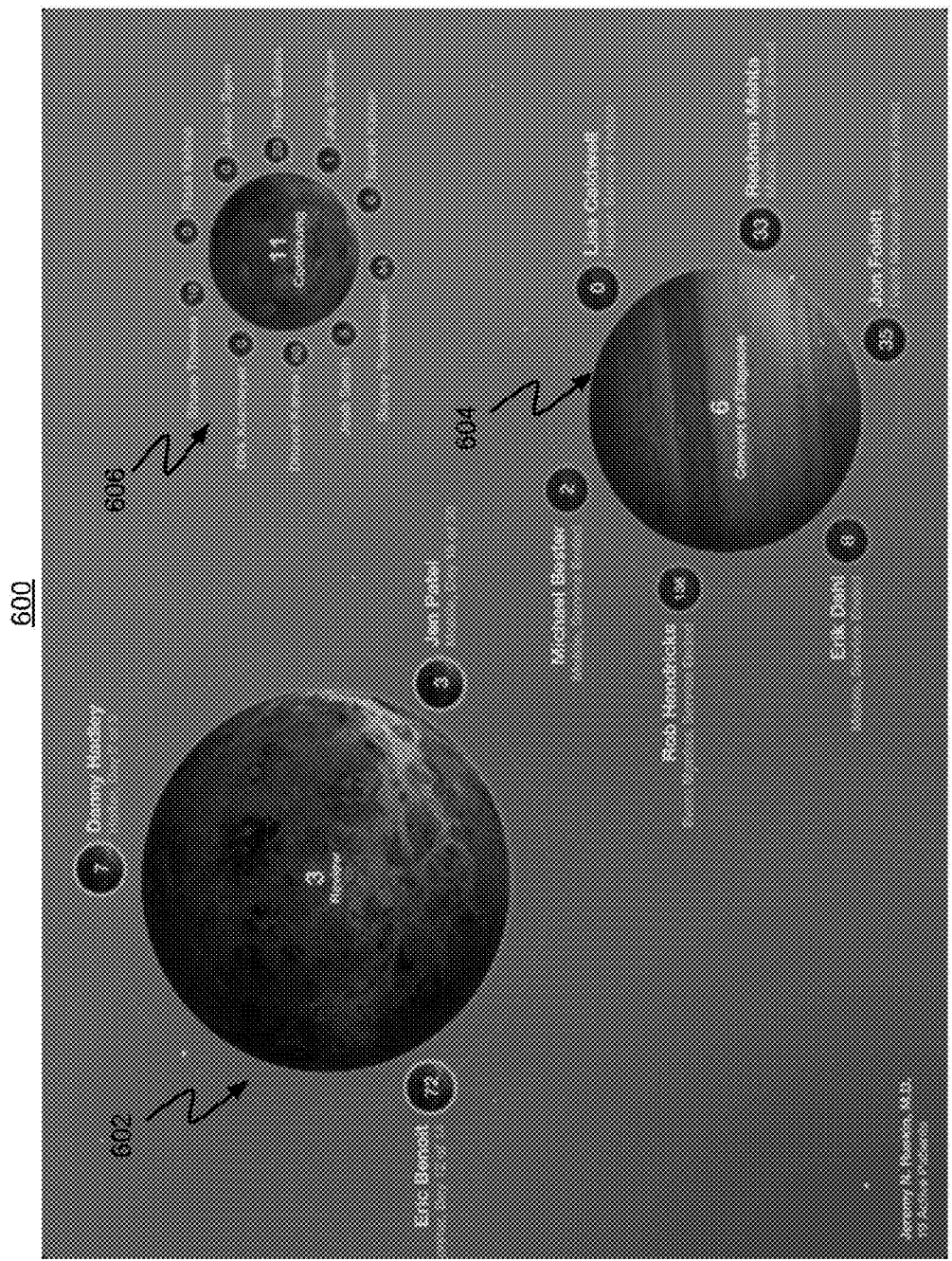
FIG. 6 is another screenshot of a physician interface for reviewing patient ECG data, according to an exemplary embodiment of the present disclosure.

FIG. 6 is another screenshot of a physician interface for reviewing patient ECG data, according to an exemplary embodiment of the present disclosure. As shown in FIG. 6, patients may be classified into one of a plurality of patient groups based on a number, recency, and/or severity of detected arrhythmic events. For example, as shown in FIG. 6, patient groups may be represented by indicia, in this case, a plurality of indicia having different colors and sizes. In one embodiment, the patient groups may include a first group for "review," including patients that have experienced an arrhythmic event within a recent time threshold, such as within the past month, week, or day, or since the physician last reviewed the interface of FIG. 6. Patient groups may include a second group for "continuing," including patients that have not experienced an arrhythmic event within a recent time threshold, such as within the past month, week, or day, or since the physician last reviewed the interface of FIG. 6. Patient groups may include a third group for "convert," or "diagnosis," including patients that have completed a prescribed monitoring period.

As shown in FIG. 6, in one embodiment, the physician interface may include a "galaxy" interface 600 including a plurality of planets functioning as indicia of each patient group, including a "review" planet 602 including three patients (represented as moons of the review planet) that have experienced arrhythmic events within a specified time period; a "convert or diagnose" planet 604 including six patients (represented as moons of the convert or diagnose planet) that have completed their prescribed monitoring period; and a "continuing" planet 606 including 10 patients (represented as moons of the continuing planet) that have not experienced arrhythmic events within a specified time period. Also as shown in FIG. 6, the "review" patient group may be represented by a relatively large and/or bright indicia, relative to a smaller and/or darker "convert or diagnose" patient group, and still smaller and/or darker "continuing" patient group. In one embodiment, all of the patients reflected in the plurality of patient groups of the "galaxy" interface of FIG. 6 may be patients of a single physician. In one embodiment, a number or other indicia may be included on each patient indicia to indicate a number of recent or total arrhythmic events experienced by the respective patient. For example, as shown in FIG. 6, the moon associated with each patient may have a number that indicates the number of arrhythmic events experienced by the patient since the patient began a monitoring period. Such a number could also or alternatively indicate a number of arrhythmic events experienced by the patient since the physician reviewed the "galaxy" interface. Again, it will be appreciated that the galaxy/planet/moon theme is only one of many suitable themes for indicia that change in color, size, and/or shape to indicate the identity and/or contents of a plurality of patient groups, based on number, severity, and/or recency of detected arrhythmic events.

In addition, indicia of each patient may reflect other attributes, such as attributes of a patient device 104 associated with each patient. For example, patient indicia reflected in interface 600 may display one or more of: a patient's compliance with device usage instructions; a patient's compliance with a prescribed treatment; a battery life of each patient's device 104; a transmitting speed and/or success of data sent from each device 104 to a network or server; and/or a connection level between device 104 and a network, cellular tower, wireless access point, or other electronic device. In addition to or instead of showing an actual level, or amount of, power charge, connection, transmission, etc., the interface 600 may display a predetermined indicia when such a value associated with the patient's device 104 has exceeded or dropped below a predetermined threshold. For example, indicia associated with a patient in interface 600 may become highlighted, bolded, outlined, or otherwise indicated as being different when, for example, a transmission level has dropped, a connection has been interrupted, a signal has been lost, a battery discharge level has been reached, etc. Thus, in addition to displaying a categorization of patients into different treatment types (e.g., review, continuing, etc.), interface 600 may also quickly and efficiently alert a physician when a user's patient device 104 is operating sub-optimally. In one embodiment, indicia of a patient displayed in interface 600 may be marked with a red or green icon, e.g., a light, to indicate a suboptimal battery level or signal level of a patent device 104. In one embodiment, a green light may indicate an acceptable battery level or signal level, whereas a red light may indicate an undesirable battery level or signal level. In one embodiment, a green light may indicate a patient's compliance with device usage instructions or a patient's compliance with a prescribed treatment, whereas a red light may indicate a patient's lack of compliance with device usage instructions or a patient's lack of compliance with a prescribed treatment.

Figure 7:
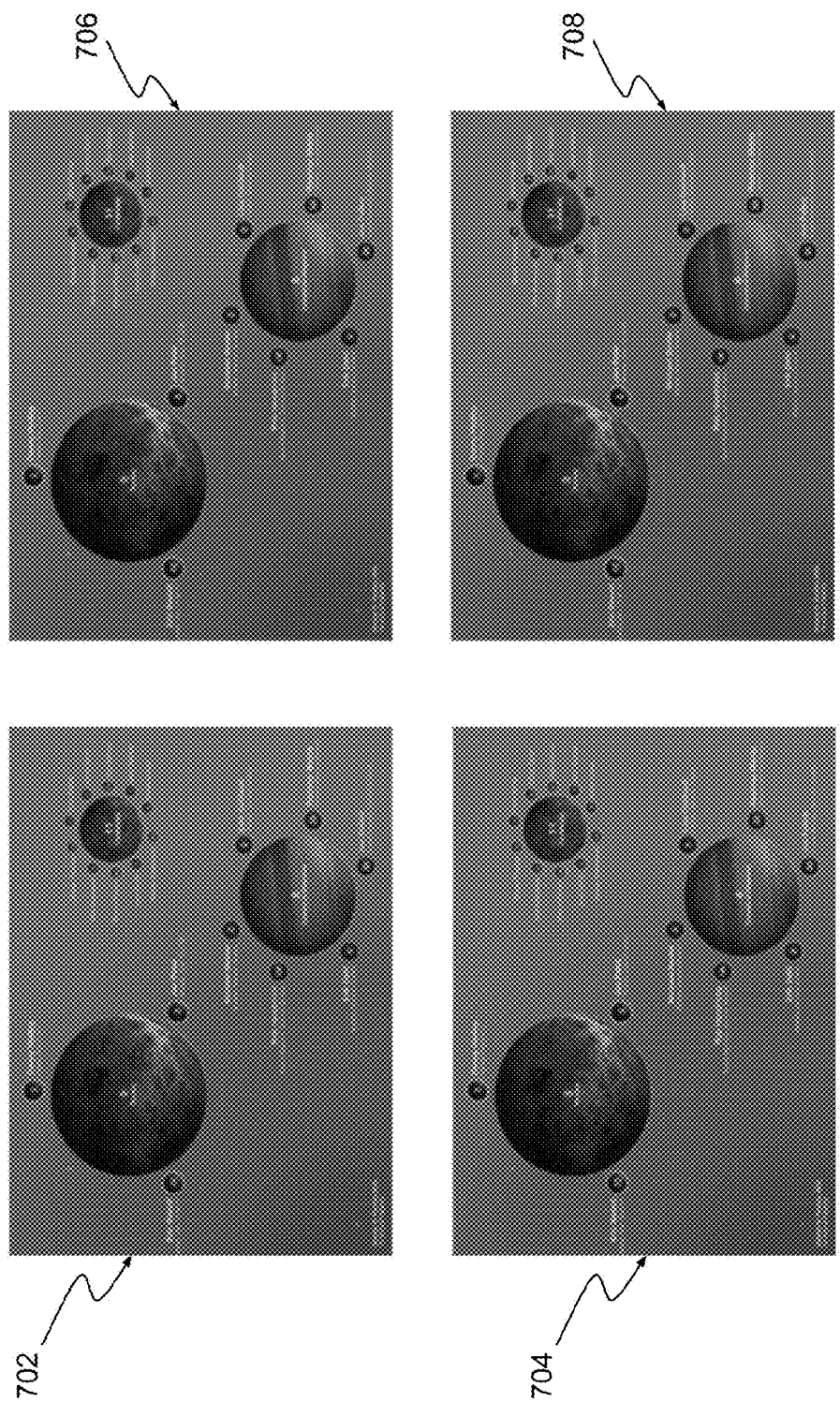
FIG. 7 is another screenshot of a physician interface for reviewing patient ECG data, according to an exemplary embodiment of the present disclosure.

FIG. 7 is another screenshot of a physician interface for reviewing patient ECG data, according to an exemplary embodiment of the present disclosure. FIG. 7 reflects that a physician may view a plurality of interfaces 702, 704, 706, 708 (e.g., separate "galaxy" interfaces as shown in FIG. 6), where each interface displays the patients of a different physician. Thus, in the "universe" view of FIG. 7, a physician may review the "galaxy" view of each physician in the physician's practice, cohort, or other collaborative group. The view of FIG. 7 provides a highly engaging, simple, and effective way for a physician to quickly identify patients of concern across a plurality of patients under the care of several physicians.

Figure 8:
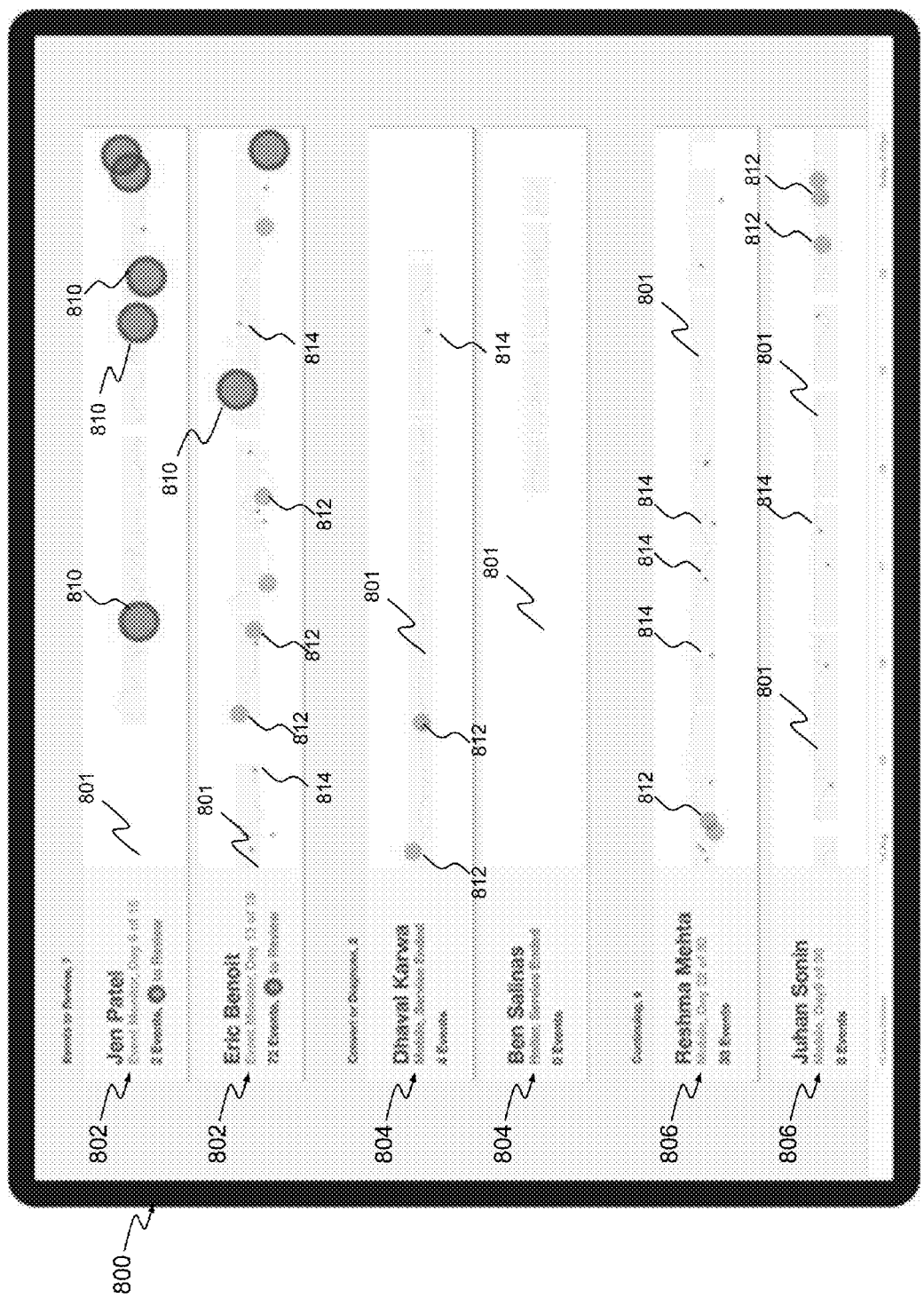
FIG. 8 is another screenshot of a physician interface for reviewing patient ECG data, according to an exemplary embodiment of the present disclosure.

FIG. 8 is another screenshot of a physician interface for reviewing patient ECG data, according to an exemplary embodiment of the present disclosure. Physician interface 800 of FIG. 8 may be configured to display ECG data and detected arrhythmic event indicia for a plurality of patients. In addition, interface 800 may be configured to sort ECG data and detected arrhythmic event indicia for the plurality of patients based on a classification of the patients into one or more of the patient groups described above, including e.g. a "review" group, "convert or diagnose" group, and "continuing" group. In one embodiment, interface 800 may first display, at a top of the interface, the patient ECG indicia 802 for patients in the "review" group because those patients have experienced an arrhythmic event within a threshold time period, and are therefore of most concern. Interface 800 may next display, after patients in the "review" group, the patient ECG indicia 804 for patients in the "convert or diagnose" group because those patients have completed their prescribed monitoring period, and should therefore be diagnosed or converted to a different type of monitoring device or treatment. Interface 800 may finally display, at the bottom of the interface, the patient ECG indicia 806 for patients in the "continuing" group because those patients have not experienced an arrhythmic event within a threshold time period, and are therefore of relatively less concern.

As shown in FIG. 8, the ECG indicia for each patient may include a plurality of different combinations of data, indicia of data, and/or indicia of conditions, e.g., arrhythmic events. For example, in one embodiment, each patient's ECG indicia may include a representation of a raw, received ECG waveform, a heart rate trend line 801, and indicia of any detected arrhythmic events displayed in relation to the ECG waveform at a position associated with a time of the detected arrhythmic event. In one embodiment, the indicia of each detected arrhythmic event may change based on a severity, type, or recency of the detected arrhythmic event. For example, as shown in FIG. 8, each arrhythmic event is shown either as a major event 810 (represented by a large, dark red circle), a moderate event 812 (represented by a medium red circle), or a minor event (represented by a small grey circle). Of course, it will be appreciated that detected arrhythmic events may be represented by any size, color, or shape of indicia, and that the size, color, or shape of the indicia may be changed in any desired way depending on any number of parameters, such as severity, type, or recency of the detected arrhythmic event. Thus, the interface 800 of FIG. 8 provides physicians with a useful, effective, and engaging way to review numerous patients under the physician's care, where the patients with the most recent and/or severe detected arrhythmic events are displayed more prominently than other patients with less recent or severe detected arrhythmic events.

In one embodiment, interface 800 may also display, for each patient, how long the patient has worn, and/or been monitored, by a device 104. For example, interface 800 may display a number of days or weeks associated with each patient, reflecting the number of days or weeks the patient has worn or been monitored by the device 104. In one embodiment, interface 800 may sort or categorize a display of patients based on the number of days or weeks the patient has worn or been monitored by the device 104.

In addition, interface 800 may indicate an activity level associated with each patient. For example, each patient device 104 may contain a GPS device, an accelerometer, and/or any other device that generates location, movement, or activity level data associated with a user. System 106 may process such received data to generate an activity level to be associated with the patient. The activity level may be a range, (e.g., low, medium, high), a percentage of prescribed or maximum activity, a numerical value associated with activity (e.g., a ranking or moving average), or a time amount associated with the activity (e.g., active for x of the past y hours). Interface 800 may then sort or categorize a display of patients based on an activity level determined for each patient. Thus, a physician may easily view interface 800 to determine relative or absolute activity levels of his or her patients to provide a better understanding of their arrhythmic, cardiac, or even general health status. In one embodiment, system 106 may generate alerts for sending to physicians when a patient's activity level reaches a certain high or low threshold, and/or when a user has worn a monitoring device for some predetermined amount of time.

In addition, interface 800 may indicate whether a patient is complying with a prescribed medication, treatment, activity, or other regimen. For example, system 106 may track each patient's compliance with a prescribed regimen, e.g., through accelerometers, blood glucose sensors, or any other biocompatible sensors. System 106 may then determine whether a patient is complying with a physician-prescribed regimen, and if desired, generate one or more alerts for sending to a physician when a patient is not in compliance with his or her prescribed regimen. For example, system 106 may alert a physician when a user is not following a prescribed drug treatment program, diet program and/or exercise program. It should be appreciated that the above-discussed indicia and related functionality (e.g., medical device battery level/signal, patient device monitoring period, patient activity level, patient compliance, etc.) may be incorporated into any of the physician interfaces described in the present disclosure.

Figure 9:
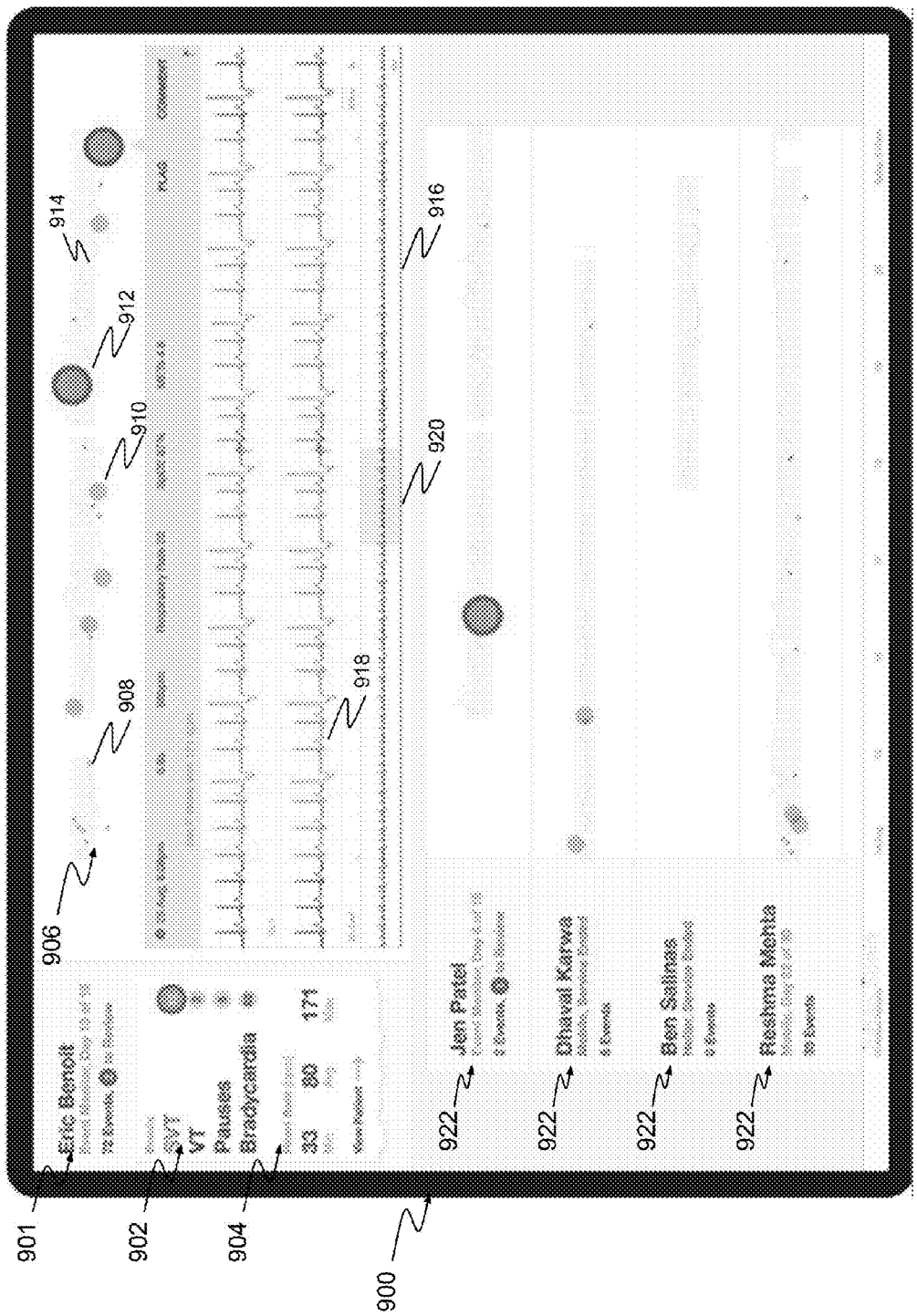
FIG. 9 is another screenshot of a physician interface for reviewing patient ECG data, according to an exemplary embodiment of the present disclosure.

FIG. 9 is another screenshot of a physician interface for reviewing patient ECG data, according to an exemplary embodiment of the present disclosure. Specifically, FIG. 9 depicts an interface 900 which provides a somewhat more detailed view of a physician interface for reviewing a patient's ECG data 901, while still also providing a limited view of ECG data 922 for other patients under the physician's care. In one embodiment, the ECG data 922 for other patients may resemble the ECG data displayed in the overview interface 800 of FIG. 8, while a more detailed ECG data 901 is displayed for the selected patient. The physician may request and therefore receive the interface view of FIG. 9 by tapping or otherwise selecting one of the patients in the interface view of FIG. 8 (e.g., the physician tapped or selected "Eric Benoit" in the view of FIG. 8 to obtain the interface view of FIG. 9). The physician may switch from a detailed view of one patient to a detailed view of another patient by tapping, swiping, or otherwise selecting one of the other patients 922 displayed in interface 900.

As shown in FIG. 9, in the detailed view of interface 900, additional ECG or other health data may be displayed for the selected patient, including a categorized list of arrhythmic events 902 (e.g., "SVT" [supraventricular tachycardia], "VT" [ventricular tachycardia], "Pauses," and "Bradycardia"), and heart rate parameters 904 (e.g., beats per minute ("bpm"), average bpm, and maximum bpm). Also, as in the interface 800, interface 900 may display the ECG waveform, heart rate trendline 914, and indicia of detected arrhythmic events in relation to the ECG waveform at a position associated with a time of the detected arrhythmic event. The indicia of detected arrhythmic events may include minor event indicia 908, moderate event indicia 910, and major event indicia 912. In addition to what is displayed in interface 800, the more detailed interface 900 may also display for the selected patient an extended ECG waveform 918, which may be a "zoomed-in" display of a subset selection 920 of an even more extended duration ECG waveform 916. The physician may then slide subset selection 920, as defined, e.g., by a shaded portion or bracket along extended duration ECG waveform 916 to change the displayed portion of zoomed-in waveform 918. The physician may also use various input methods to expand or compress the subset selection 920, such as by squeezing or pinching a touchscreen interface of the physician device 102. In one embodiment, various portions of the extended waveform 918 or waveform 916 may be highlighted, darkened, bolded, or otherwise indicated as being associated with an arrhythmic event. Accordingly, the interface 900 may prompt a physician to investigate and review various heart parameters, statistics, and ECG data associated with events of significant import.

Figure 10:
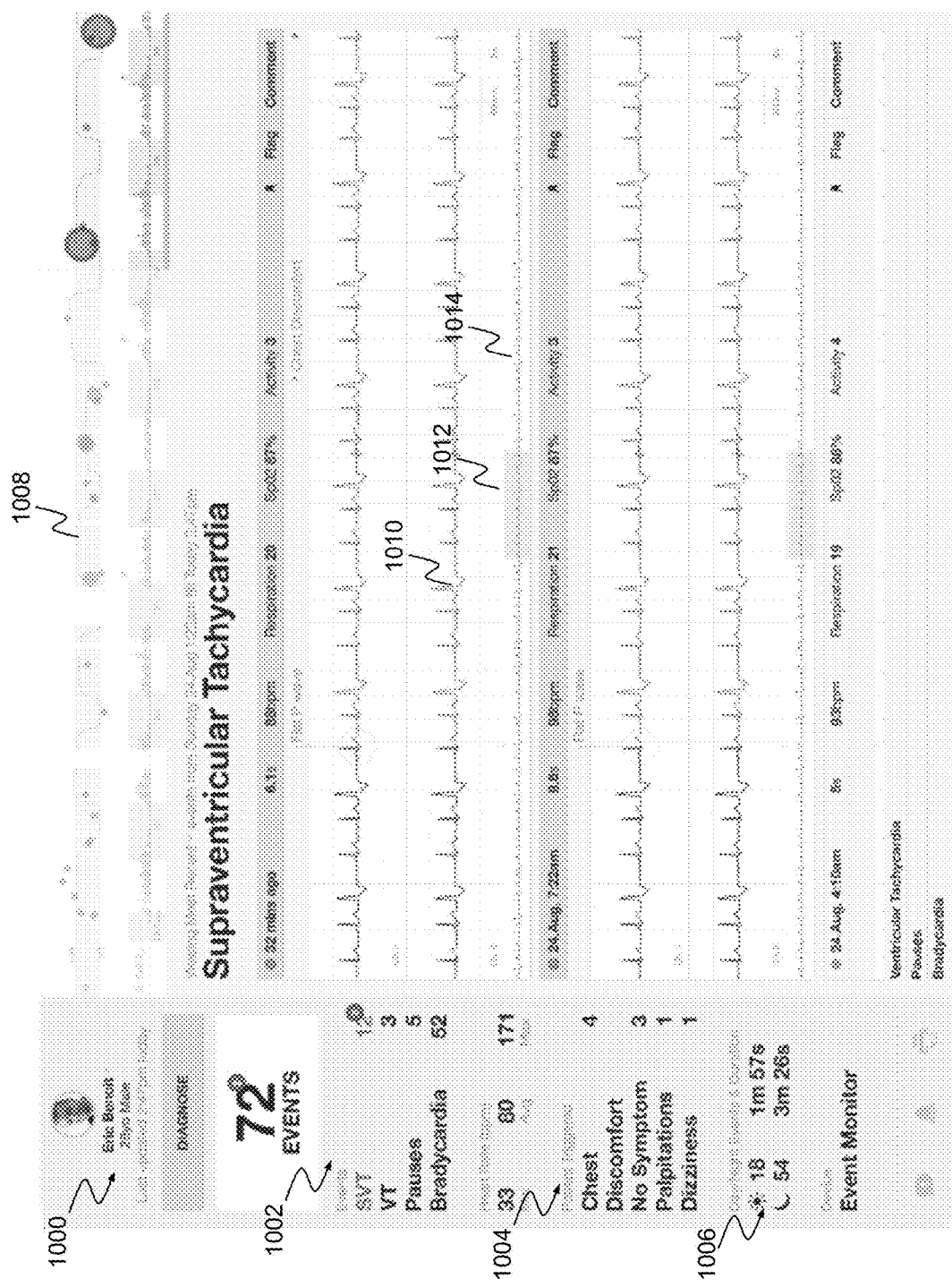
FIG. 10 is another screenshot of a physician interface for reviewing patient ECG data, according to an exemplary embodiment of the present disclosure.

FIG. 10 is another screenshot of a physician interface for reviewing patient ECG data, according to an exemplary embodiment of the present disclosure. Specifically, FIG. 10 depicts an even more detailed interface 1000 of a specific patient under review. Interface 1000 may again include arrhythmic events 1002 (e.g., "SVT," "VT," "Pauses," and "Bradycardia"), and heart rate parameters (e.g., beats per minute ("bpm"), average bpm, and maximum bpm), but also patient-triggered complaints 1004 (e.g., "chest discomfort," "palpitations," "dizziness," etc.) associated with each arrhythmic event. In addition, detailed interface 1000 may also categorize detected arrhythmic events into day/night events 1006, based on the number and/or duration of the events, to assist a physician in associating events with certain day or night activities, and for facilitating proposed treatments or interventions. As in the interface 900 of FIG. 9, interface 100 may also include a heartrate trendline 1008, and an extended ECG waveform 1010 defined by subset selection 1012 of further extended ECG waveform 1014. Also, as in interface 900, a physician may interact with a touchscreen of physician device 102 to manipulate subset selection 1012 to identify, investigate and review various heart parameters, statistics, and ECG data associated with arrhythmic events of significant import.

In one embodiment, in addition to identifying arrhythmic events, as described above, a physician may add to a patient's ECG data any other event or timeframe of interest to the physician or relevance to the patient's health. For example, a physician may associate with a patient's ECG data the date or time at which an ablation treatment procedure was performed on a patient. Thus, the physician may define a timeframe preceding the indicated ablation procedure as containing pre-ablation ECG data, and a timeframe following the indicated ablation procedure as containing post-ablation ECG data. Any of the interfaces disclosed herein may then enable a physician to view, analyze, sort, and compare patient ECG data in relation to pre- and post-ablation time periods. Physicians may perform similar techniques for any other treatment procedure relevant to patient cardiac health.

Categorizing and sorting ECG data relative to a timeframe of a medical procedure may assist physicians in evaluating the effectiveness of the medical procedure. For example, a physician may generate a report, and/or display on opposing sides of a display device, ECG data for time periods preceding and following a medical procedure, such as an ablation procedure for treating arrhythmia. A physician may then more easily compare ECG data and arrhythmic events between different time frames. Relevant time frames may also be segmented, cross-referenced, or normalized by, e.g., time-of-day, activity level, blood pressure, etc. For example, a physician may compare a patient's morning, pre-ablative ECG data to the patient's morning, post-ablative ECG data. Alternatively, a physician may compare a patient's pre-ablative, post-exercise ECG data to the patient's post-ablative, post-exercise ECG data. It will be appreciated that any combination of timeframes, based on treatment periods or events, heart rate periods or events, or any other timeframe of interest may be used to generate a display of ECG data for a physician to view through any of the presently-disclosed interfaces.

Although embodiments of the present invention have been described as detecting and verifying suspected arrhythmias, other embodiments may be similarly configured and used to detect and verify other health or fitness conditions, such as inappropriate insulin level, respiration, blood pressure, SpO2, body movement, exertion and the like.

A remote health monitoring system may include a processor controlled by instructions stored in a memory. For example, the transceiver assembly may include and be controlled by such a processor, and the remote server may be controlled by another such processor. The memory may be random access memory (RAM), read-only memory (ROM), flash memory or any other memory, or combination thereof, suitable for storing control software or other instructions and data.

Some of the functions performed by the remote health monitoring system have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof.

Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer network.

In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for displaying ECG data associated with a plurality of members on a display screen of an electronic device, the method comprising:

classifying the plurality of members into multiple groups based on the ECG data, the multiple groups including a first group and a second group;

displaying in a first image on the screen, pictorial representations of the first group and the second group, wherein one or more attributes of the pictorial representation of the first group represent distinguishing features of the ECG data of the members of the first group compared to the ECG data of the members of the second group; and displaying in the first image, a pictorial representation of at least one member of the first group separate from the pictorial representation of the first group, wherein one or more attributes of the pictorial representation of the at least one member represent distinguishing features of the ECG data of the at least one member compared to the ECG data of other members in the first group, wherein the pictorial representation of the at least one member includes an indication of at least one of (a) a severity of a health-related event detected from the ECG data, (b) a recency of a health-related event detected from the ECG data, and (c) a number of health-related events detected from the ECG data.

2. The method of claim 1, wherein at least one of a size, a color, or a shape of the pictorial representation of the first group is different from the pictorial representation of the second group.

3. The method of claim 1, wherein the pictorial representation of the at least one member of the first group is positioned outside a periphery of the pictorial representation of the first group.

4. The method of claim 1, wherein classifying the plurality of members into multiple groups includes grouping members based on a characteristic of the ECG data associated with each member of the plurality of members.

5. The method of claim 1, wherein a color of the pictorial representation of the at least one member identifies a difference in the ECG data of the at least one member compared to the ECG data of other members of the first group.

6. The method of claim 1, wherein the members include patients.

7. The method of claim 6, further comprising analyzing the ECG data to detect arrhythmic events.

8. The method of claim 1, wherein the pictorial representation of the first group is spaced apart from the pictorial representation of the second group.

9. The method of claim 1, wherein the pictorial representation of the at least one member identifies a battery level of a device used to measure the ECG data of the at least one member.

10. The method of claim 1, wherein the pictorial representation of the at least one member indicates the at least one member's compliance with prior instructions.

11. The method of claim 1, wherein the multiple groups additionally include a third group, wherein (a) the first group includes members that have experienced a condition within a selected time period, (b) the second group includes members that have not experienced the condition within a second time period, and (c) the third group includes members that have completed a preselected monitoring period.

12. The method of claim 1, further including:
modifying the first image based on input received from a user; and
displaying the modified first image on the screen.

13. A system for displaying ECG data associated with a plurality of members on a screen, the system comprising:
a data storage device storing instructions for displaying; and
a processor configured to execute the instructions and perform a method comprising:
classifying the plurality of members into multiple groups based on the ECG data, the multiple groups including a first group and a second group;
displaying in a first image on the screen, pictorial representations of the first group and the second group, wherein one or more attributes of the pictorial representation of the first group represent distinguishing features of the ECG data of the members of the first group compared to the ECG data of the members of the second group; and
displaying in the first image, a pictorial representation of at least one member of the first group separate from the pictorial representation of the first group, wherein one or more attributes of the pictorial representation of the at least one member represent distinguishing features of the ECG data of the at least one member compared to the ECG data of other members in the first group, wherein the pictorial representation of the at least one member includes an indication of at least one of (a) a severity of a health-related event detected from the ECG data, (b) a recency of a health-related event detected from the ECG data, and (c) a number of health-related events detected from the ECG data.

14. The system of claim 13, wherein the members include patients.

15. The system of claim 14, further comprising analyzing the ECG data to detect arrhythmic events.

16. The system of claim 13, wherein at least one of a size, a color, or a shape of the pictorial representation of the first group is different from the pictorial representation of the second group.

17. The system of claim 13, wherein the pictorial representation of the first group is spaced apart from the pictorial representation of the second group, and the pictorial representation of the at least member of the first group is positioned outside a periphery of the pictorial representation of the first group.

18. The system of claim 13, wherein the plurality of groups further include a third group, wherein (a) the first group includes members that have experienced a condition within a selected time period, (b) the second group includes members that have not experienced the condition within the selected time period, and (c) the third group includes members that have completed a preselected monitoring period.

19. A handheld device for displaying ECG data associated with a plurality of members, the handheld device comprising:
a display device for displaying representations of the ECG data on a screen;
a memory device storing instructions for the displaying; and
a processor configured to execute instructions for:
classifying the plurality of members into multiple groups based on the ECG data, the multiple groups including a first group and a second group;
displaying in a first image on the screen, pictorial representations of the first group and the second group, wherein one or more attributes of the pictorial representation of the first group represent distinguishing features of the ECG data of the members of the first group compared to the ECG data of the members of the second group; and
displaying in the first image, a pictorial representation of at least one member of the first group separate from the pictorial representation of the first group, wherein one or more attributes of the pictorial representation of the at least one member represent distinguishing features of the ECG data of the at least one member compared to the ECG data of other members in the first group, wherein the pictorial representation of the at least one member includes an indication of at least one of (a) a severity of a health-related event detected from the ECG data, (b) a recency of a health-related event detected from the ECG data, and (c) a number of health-related events detected from the ECG data.

20. The device of claim 19, wherein:
(a) at least one of a size, a color, or a shape of the pictorial representation of the first group is different from the pictorial representation of the second group;

(b) the pictorial representation of the first group is spaced apart from the pictorial representation of the second group; and
(c) the pictorial representation of the at least one member of the first group is positioned outside a periphery of the pictorial representation of that group.

\* \* \* \* \*